United States Patent
Chang et al.

(10) Patent No.: US 6,479,105 B2
(45) Date of Patent: *Nov. 12, 2002

(54) METHOD OF MAKING A FLUSHABLE FILM HAVING BARRIER PROPERTIES

(75) Inventors: Yihua Chang, Appleton, WI (US); John Edward Kerins, Neenah, WI (US); William Seal Pomplun, Neenah, WI (US); Stephen M. Campbell, Winneconne, WI (US)

(73) Assignee: Kimberly Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/844,210

(22) Filed: Apr. 30, 2001

(65) Prior Publication Data

US 2001/0021458 A1 Sep. 13, 2001

Related U.S. Application Data

(62) Division of application No. 09/210,015, filed on Dec. 11, 1998, now abandoned.

(51) Int. Cl.[7] .......................... B05D 5/08; A61F 15/15; B32B 9/00; B32B 31/00
(52) U.S. Cl. .................. 427/385.5; 427/375; 604/364; 428/41.8; 156/289
(58) Field of Search ............................... 156/230, 231, 156/241, 247, 289; 427/146, 147, 148, 385.5, 375; 428/41.8, 40.1, 364, 352, 335, 461, 914; 604/364, 378

(56) References Cited

U.S. PATENT DOCUMENTS

| | | |
|---|---|---|
| 3,654,928 A | 4/1972 | Duchane |
| 3,683,917 A | 8/1972 | Comerford |
| 4,186,233 A | 1/1980 | Krajewski et al. |
| 4,229,239 A | 10/1980 | Arai |
| 4,269,650 A | 5/1981 | Arai |
| 4,372,311 A | 2/1983 | Potts |
| 4,416,791 A | 11/1983 | Haq |
| 4,610,685 A | 9/1986 | Raley |
| 4,654,395 A | 3/1987 | Schulz |
| 4,655,868 A | 4/1987 | Hefele |
| 4,705,584 A | 11/1987 | Lauchenauer |
| 4,731,143 A | 3/1988 | Cross |
| 4,762,738 A | 8/1988 | Keyers et al. |
| 4,868,024 A | 9/1989 | Cross et al. |
| 4,868,051 A | 9/1989 | Grosjean |
| 4,887,321 A | 12/1989 | MacLean |
| 5,108,382 A | 4/1992 | Wright et al. |
| 5,110,390 A | 5/1992 | Martini et al. |
| 5,130,290 A | 7/1992 | Tanimoto |
| 5,158,810 A | 10/1992 | Oishi et al. |
| 5,236,493 A | 8/1993 | Hunter et al. |
| 5,283,090 A | 2/1994 | Umemura |
| 5,300,358 A | 4/1994 | Evers |
| 5,318,730 A | 6/1994 | Reiser et al. |
| 5,322,866 A | 6/1994 | Mayer et al. |
| 5,468,526 A | 11/1995 | Allen et al. |
| 5,476,457 A | 12/1995 | Roessler et al. |
| 5,496,295 A | 3/1996 | Wilfong et al. |
| 5,509,913 A | 4/1996 | Yeo |
| 5,527,303 A | 6/1996 | Milby, Jr. et al. |
| 5,529,830 A | 6/1996 | Dutta |
| 5,567,488 A | 10/1996 | Allen et al. |
| 5,578,344 A | 11/1996 | Ahr et al. |
| 5,613,959 A | 3/1997 | Roessler et al. |
| 5,827,214 A | 10/1998 | Fox et al. |
| 5,981,012 A * | 11/1999 | Pomplun et al. ........... 428/41.8 |
| 5,985,396 A | 11/1999 | Kerins et al. |

FOREIGN PATENT DOCUMENTS

| | | |
|---|---|---|
| EP | 0 079 248 | 5/1983 |
| EP | 0 461 484 | 12/1991 |
| EP | 0479404 | 4/1992 |
| GB | 2083762 | 3/1982 |
| GB | 2185404 | 7/1987 |
| JP | 4-40948 | 2/1992 |
| WO | WO 91/14413 | 10/1991 |

* cited by examiner

Primary Examiner—J. A. Lorengo
(74) Attorney, Agent, or Firm—Kilpatrick Stockton LLP

(57) ABSTRACT

The present invention provides a composition comprising a low-molecular weight, amorphous polyalphaolefin layer and a water-sensitive substrate layer. Preferably, the polyalphaolefin comprises either a propylene-ethylene copolymer or an ethylene-butene copolymer. Polyalphaolefin coated water-dispersible films of the present invention may be advantageously employed in the preparation of a wide variety of products designed to be contacted with aqueous fluids. Although the coated water-dispersible film of the present invention is particularly suited for personal care products, the coated water-dispersible film of the present invention may be advantageously employed in the preparation of a wide variety of consumer products other than personal care products. When the entire product is disposed of in water, the water-sensitive layer is wetted and weakens. Since the polyalphaolefin layer is already mechanically weak, hydraulic force from a toilet flow causes the composition to disperse into pieces small enough to flow through the toilet and beyond without clogging the water system.

9 Claims, No Drawings

METHOD OF MAKING A FLUSHABLE FILM HAVING BARRIER PROPERTIES

The present application is a divisional application of U.S. Ser. No. 09/210,015, filed on Dec. 11, 1998 now abandoned.

FIELD OF THE INVENTION

The present invention relates to polymer compositions that are water stable on one surface and water-sensitive on the opposing surface. More particularly, the present invention encompasses flushable films that retain their integrity in the presence of body waste fluids, but which disintegrate and disperse in the hydraulic flow of a toilet.

BACKGROUND OF THE INVENTION

Disposable products have revolutionized modem lifestyle and are of great convenience to society. Such products generally are relatively inexpensive, sanitary and quick and easy to use. Disposal of such products, however, increasingly is a problem as landfills close and incineration contributes to urban smog and pollution. Consequently there is an urgent need for disposable products that can be disposed of without dumping or incineration. An ideal disposal alternative would be the use of municipal sewage treatment and private residential septic systems. Products suited for disposal in sewage systems that can be flushed down a conventional toilet are termed "flushable." An essential feature of flushable products is that they must have sufficient strength for their intended use, yet lose structural integrity upon contact with water.

Numerous attempts have been made to produce flushable fibers, fabrics, films and adhesives that retain their integrity and wet strength in the presence of body waste fluids, yet can be disposed of via flushing in conventional toilets. One approach to producing a flushable product is to limit the size of the product so that it will readily pass through plumbing without causing obstructions or blockages. Such products often have high wet strength and do not disintegrate during flushing. Examples of this type of product include wipes such as baby wipes. This approach to flushability suffers the disadvantage, however, of being restricted to small articles.

Another approach to producing a flushable product is to manufacture a product that is normally insoluble in water, but which disintegrates in the presence of alkaline or acidic aqueous solutions. The end user is provided with an alkaline or acidic material to add to the water in which the product is to be disposed. This approach permits disposal via normal plumbing systems of products substantially larger than wipes, but suffers from the disadvantage of requiring the user to perform the step of adding the dissolving chemical to the water. A further disadvantage is that the inadvertent or intentional disposal of such a product in a conventional toilet without the addition of the dissolving chemical can cause serious obstruction or blockage of the plumbing system. The latter disadvantage can, however, be overcome by incorporating the dissolving acid or alkali into the article but separate from the dissolvable material while in use. The dissolving chemical is only released upon contact with water during flushing.

Similarly, another approach to producing a flushable product, particularly wipes, consists of forming the product from a pH-sensitive gelled polymer, and storing the product in the presence of a separate acidic solution. When the wipe is placed in a large quantity of neutral pH water, it disintegrates as a result of the pH shift. A disadvantage of this pH shift approach to flushability is that some acidic polymers lose wet strength at slightly alkaline pH in the range of 7–8. Because the pH of urine may be as high as 8.5, these flushable materials are not well suited for use in, for example, diapers or incontinence pads.

Another approach to producing a flushable product is to form the product from material that is susceptible to attack by specific enzyme catalysis that breaks down the structural integrity of the material. In such a product the enzymes may be introduced into the disposal water separately. These systems suffer many of the same disadvantages as those described above for alkaline or acid treatable materials.

UK patent application GB 2 083 762A to Enak Limited discloses an ostomy pouch where a water impermeable layer of polyvinylidene chloride, vinyl chloride-vinylidene chloride-copolymer, atactic polypropylene, nitrocellulose, waxes, greases, silicone, or pressure sensitive adhesives is backed by a layer of polyethylene oxide or polyvinyl alcohol. However, this construction may not be mechanically weak enough in the flow of toilet water to disintegrate sufficiently.

UK patent application GB 2 185 404A to Smiths Industries Public Limited Co. discloses an ostomy bag with an inner layer of polyvinylidene chloride is backed by a layer of polyvinyl alcohol. However, this construction may not be mechanically weak enough in the flow of toilet water to disintegrate sufficiently.

U.S. Pat. No. 4,732,311 to J. E. Potts discloses coating a water soluble polymer, such as polyethylene oxide with a degradable water-insoluble polymer such as a cyclic ester polymer, a poly(beta-hydroxy butyrate), dialkanoyl polymers, such as polyesters and polyurethanes derived from aliphatic polyols, and ethylene polymers.

U.S. Pat. No. 5,283,090 to Y. Umemura discloses a multi-layered urine or ostomy bag, the inner side of which is water-impermeable by means of silicon or fluorine-containing coatings such as polytetrafluoroethylene and methylhydroxypolysiloxane. The sheet may be made of polyvinylpyrrolidine, polyacrylamide, polyvinyl ethers, polyethylene oxide, methyl cellulose, ethyl cellulose, carboxymethyl cellulose, hydroxyethyl cellulose, polyvinyl alcohol, polyacrylic acid and polymethacrylic acid, and isobutene-maleic acid copolymers.

U.S. Pat. No. 5,110,390 to F. Martini, et al., discloses an ostomy bag of a laminate of a water-disintegratable film such as polyvinyl alcohol or polyethylene oxide, and a coextruded film of vinylidene chloride polymer or ethylene copolymer which includes a melt-bondable layer.

U.S. Pat. No. 5,300,358 to G. R. Evers discloses a flushable structure for absorption of body fluids composed of an absorbent degradable fibrous core and a backsheet that is cold-water soluble, but water impermeable.

U.S. Pat. No. 5,468,526 to S. I. Allen, et al., discloses an ostomy bag composed of a homopolymer of vinylidene chloride or methylmethacrylate coated onto a water soluble film layer of a blend of polyvinyl alcohol, polycaprolactone, or polyethyloxazoline and a thermoplastic polyurethane.

U.S. Pat. No. 5,578,344 to N. A. Ahr, et al., discloses a process for impregnating a resin onto a substrate to form a web, where the exposed side of the web is dispersible in water, while the impregnated side is water resistant.

None of the above methods and articles have proven entirely satisfactory. Therefore, there is a need for a flushable product which is not limited in size and which does not require special conditions of disposal.

SUMMARY OF THE INVENTION

The present invention provides a composition comprising a low-molecular weight, amorphous polyalphaolefin layer and a water-sensitive substrate layer. Preferably, the polyalphaolefin is a poly(propylene-ethylene) copolymer or a poly(ethylene-butene) copolymer. When the composition is employed as a diaper outer cover or a pantiliner baffle, for example, the polyalphaolefin layer is exposed to bodily fluids, and inhibits their transport to the water-sensitive layer. When the entire article is disposed of in a toilet, however, the water-sensitive layer is wetted and weakens. Since the low-molecular weight amorphous polyalphaolefin layer is already mechanically weak without the support of the water-sensitive layer, the hydraulic force of the toilet flow causes the composition to disperse into pieces small enough to flow through the toilet and beyond without clogging the water system.

It is, therefore, desirable to provide disposable products that can be flushed in a conventional toilet with subsequent product dispersion into pieces that can be managed by standard sewage treatment or home septic systems. Additionally, it is desired to provide disposable products that can be flushed in a conventional toilet without the addition of a dissolving chemical. Finally, it is desired to provide flushable products that are insoluble in the presence of body waste fluids, but which are water soluble in the presence of normal toilet water.

DETAILED DESCRIPTION OF THE INVENTION

Polyalphaolefins are widely used as adhesives. However, their value as a barrier layer for a water-sensitive substrate has not been previously recognized. The inventors have discovered that these polyalphaolefins provide an effective barrier layer against fluids, thereby permitting films having a layer of a polyalphaolefin to be used in a variety of different applications, such as disposable personal care products.

The present invention provides a two-layer film composition, comprising a low molecular weight amorphous polyalphaolefin layer joined to a water-dispersible substrate layer. In general, a melt viscosity in excess of 10,000 cps at 190° C. is indicative of higher molecular weight polyalphaolefins, while a melt viscosity of less than 10,000 cps at 190° C. is indicative of low molecular weight polyalphaolefins. Desirably, amorphous polyalphaolefins useful in the present invention are low molecular weight polyalphaolefins having a melt viscosity of about 400 to about 10,000 cps at 190° C. Preferably, the polyalphaolefin comprises propylene-ethylene copolymers or ethylene-butene copolymers. The compositions of the present invention have sufficient strength for their intended use, yet are dispersible into pieces under the hydraulic force of normal tap flow or toilet water flow.

Films of the present invention can be widely used as components of such disposable goods as sanitary napkins, pantiliners, diapers, bandages, and the like. Such films, if they are to function effectively, must maintain their structural integrity, as well as exhibit satisfactory tensile strength, when they are wet or damp with various body fluids. These body fluids include blood, menstrual fluid, vaginal exudate, urine and perspiration, which the films will contact during use. It has been recognized that if such films, while retaining their strength in body fluids, were to lose their integrity when exposed to water and become readily dispersible therein, disposal problems would be substantially eliminated, since the films could be easily and conveniently disposed of by contacting the film with water. The present invention provides a mechanism for eliminating disposal problems associated with various consumer products.

The present invention can be described as a flushable film composition comprising a layer of a hydrophobic, low molecular weight, amorphous polyalphaolefin resin joined to a water-dispersible substrate. The polyalphaolefin layer preferably comprises propylene-ethylene copolymers or ethylene-butene copolymers. The compositions of the present invention can further comprise an absorbent layer of material adjacent the hydrophobic, polyalphaolefin layer opposite the side joined to the water-dispersible substrate layer. The absorbent layer can comprise synthetic and natural materials well-known in the field of diapers and pantiliners for example, which are generally very fibrous, porous and hydrophilic.

In a further embodiment of the present invention, the film composition may serve as a primer layer for additional coatings on the water-dispersible substrate, such as latex coatings. The primer layer provides enough water protection so that a water-based solution coating may be applied to the coated water-dispersible film, the water being subsequently removed prior to any degradation of the water-dispersible substrate layer. In most cases and applications, the coated water-dispersible film is flushable because it will disperse rapidly when exposed to the hydraulic water flow in a conventional toilet.

The term "flushable" as used herein means capable of being flushed in a conventional toilet, and being introduced into a municipal sewage or residential septic system, without causing an obstruction or blockage in the toilet or sewage system.

The term "amorphous" as used herein means a polymer having a degree of crystallinity of less than about 20%. Since the polyalphaolefin layer of the present invention is amorphous and of a low-molecular weight, it is weak, and the thin coating breaks apart very easily when the water-dispersible substrate begins to disperse. The amorphous character of the polyalphaolefin layer precludes any substantial crystal formation, and any associated crystalline brittleness in the coating. The amorphous character also provides adhesive tack for the coating to adhere well to the water-dispersible substrate.

The polyalphaolefin coated water-dispersible films of the present invention may be used in the preparation of a wide variety of products designed to be contacted with aqueous fluids. Although the coated water-dispersible film of the present invention is particularly suited for personal care products, the coated water-dispersible film of the present invention may be advantageously employed in the preparation of a wide variety of consumer products other than personal care products.

For a flushable composition of the present invention, such as a diaper outer cover or a pantiliner baffle, the inner side of the composition—the side closer to the wearer of the article—will typically be exposed to body fluids in use, while both sides will be exposed to toilet water in disposal. The polyalphaolefin coating on the side adjacent to the wearer of the article inhibits the transport of body fluids through the composition, and provides a barrier between body fluids and the water-dispersible substrate on the outer surface. However, the side of the article further from the wearer of the water-dispersible substrate is designed to quickly weaken in the flow of toilet water, and allows the entire composition to lose enough structural integrity to flush down a conventional toilet. Preferably, the substrate has a peak-load strength of less than 20 g/in, which is comparable to wet bathroom tissue.

A coating of a low molecular weight amorphous polyalphaolefin polymer provides a substantial barrier to body fluids, yet has very little mechanical strength. It therefore loses its mechanical integrity when the water-dispersible substrate disperses in the hydraulic flow of plain toilet water. Desirably, the low molecular weight amorphous polyalphaolefin has a melt viscosity of about 400 to about 10,000 cps at 190° C. As a polyalphaolefin, the coating is hydrophobic, and so provides a good water barrier even in thin layers. The invention provides that the amorphous polyalphaolefin layer can be between about 0.1 to 5 mils thick, and preferably about 0.5 to 2.0 mils thick. The low molecular weight and relative thinness ensure that the coating has little mechanical integrity of its own; little force is required to pull the coating into pieces, as measured in a test of wet tensile strength.

Amorphous polyalphaolefin polymers that can be used in the present invention include, but are not limited to, propylene-ethylene copolymers and ethylene-butene copolymers. Desirable polyalphaolefin polymers include REXTAC® polymers, which are available from the Rexene Corporation (Dallas, Tex. 75244) under the designation RT2315, RT2535. In general, the REXTAC® polymers are low density (0.86 to 0.88 g/cc), low molecular weight polyalphaolefins. Each of the REXTAC® polymers has a melt viscosity of from about 400 to about 10,000 cps at 190° C. and a tensile strength of from about 0.25 to about 1.5 MPa.

Suitable polymers for the water-dispersible substrate layer include, but are not limited to, polyalkylene oxides, such as polyethylene oxide (PEO), ethylene oxide-propylene oxide copolymers, polymethacrylic acid, polymethacrylic acid copolymers, polyvinyl alcohol, polyethyl oxazoline, polyvinyl methyl ether, polyvinyl pyrrolidone/vinyl acetate copolymers, methyl cellulose, ethyl cellulose, hydroxypropyl cellulose, hydroxypropyl methyl cellulose, ethyl hydroxyethyl cellulose, methyl ether starch, poly (n-isopropyl acrylamide), poly N-vinyl caprolactam, polyvinyl methyl oxazolidone, polyvinyl methyl oxazolidimone, poly(2-isopropyl-2-oxazoline), and poly (2,4-dimethyl-6-triazinyl ethylene).

The water-dispersible substrates of the present invention may be made entirely of water-dispersible polymeric material or may contain water-dispersible as well as water-insoluble materials so long as the film disperses in water, such as in the hydraulic flow of a conventional toilet. Additionally, water-dispersible films may also be made by mixing various different types of water-dispersible film materials. In some embodiments, it may be desirable to employ one or more additives into the water-dispersible film material including, but not limited to, compatibilizers, processing aids, plasticizers, tackifiers, detackifiers, slip agents, and anti-microbial agents, as fabricating agents or as modifiers depending on the specific properties desired in the film and the final product.

Additionally, in another embodiment, the amorphous, low molecular weight polyalphaolefin may be admixed with a paraffin wax, such as a highly branched hydrocarbon. These hydrocarbons help to lower the wet strength of the film while maintaining barrier strength. One such paraffin wax is VYBAR® 253 polymer from Petrolite Corp. (Tulsa, Okla.). Preferably, the wax is admixed in an amount from about 1 to about 20 percent by weight. More preferably, the wax is admixed in an amount of about 10 percent by weight.

Desirably the water-dispersible film of the present invention comprises a polyalkylene oxide film or a polyvinyl alcohol film. More desirably, the water-dispersible film of the present invention comprises a polyethylene oxide film, an ethylene oxide-propylene oxide copolymer film, a polyvinyl alcohol film or a film derived from a polyvinyl alcohol copolymer. Most desirably, the water-dispersible film of the present invention comprises a polyethylene oxide film or a polyvinyl alcohol film. The polyethylene oxide film is the most desirable film for a transfer coating procedure, while the polyvinyl alcohol film is the most desirable film for a direct coating procedure. The thickness of the water-dispersible film may vary greatly depending upon the end use of the film-containing product. Film thickness should be minimized when possible to reduce product cost and to reduce the time necessary for the film to disperse, especially in the case of flushable products. Desirably, the water-dispersible substrate will be between about 0.1 to 10 mils thick, or more desirably about 1 to 2 mils thick.

The polyalphaolefin layer may be joined to the water-dispersible substrate by standard methods known to those of ordinary skill in the art. As mentioned, the polyalphaolefin layer itself can provide enough tack to join the water-sensitive substrate layer thereto. Other suitable methods of joining the layers include, but are not limited to, solvent-based coating and hot-melt coating. Suitable solvent-based coating techniques include, but are not limited to, spray coating and ink jet printing. Suitable hot-melt coating techniques include, but are not limited to, slot coating, screen coating, spray coating, swirl coating and gravure coating. Another suitable method includes a transfer coating procedure.

The preferred coating process is a hot-melt slot die process. Molten polyalphaolefin polymer is delivered from a melting tank through a heated hose to a slot die. The temperature of the melting tank, hose and slot die may vary depending upon the melt rheology of the polyalphaolefin in the coating process. The molten polymer is uniformly applied directly onto the water-sensitive film, or alternatively, onto a carrier substrate and subsequently transferred onto the water-sensitive film (transfer coating process). Line speeds may vary depending upon the "open time" of the polyalphaolefin. As used herein, the "open time" of a polymer refers to the amount of time required for the polymer to lose its tackiness.

In a transfer coating process, the coated carrier substrate moves further through the process and comes into contact with the water-sensitive film, which is properly aligned with the coated carrier substrate. The coating is transferred from the carrier substrate to the water-sensitive film under pressure as the film and carrier substrate pass through a nip roll. In practice, optimum coating thickness is achieved by adjusting processing factors which include, but are not limited to, the polyalphaolefin, the coating temperature, the resin flow rate, line speed, and the pressure applied at the nip roll.

In the transfer coating process or in a contact direct coating process, such as screen printing, the adhesion of the polyalphaolefin coating to the water-sensitive film should be greater than the adhesion of the polyalphaolefin coating to the screen (direct coating) or the carrier substrate (transfer coating). The choice of polyalphaolefin should take into consideration the desired characteristics and properties of the polyalphaolefin. The polyalphaolefin should have good adhesion to the water-sensitive substrate.

Those skilled in the art will readily understand that the polyalphaolefin coated water-dispersible films of the present invention may be advantageously employed in the preparation of a wide variety of products designed to be contacted with aqueous fluids. Although the coated water-dispersible film of the present invention is particularly suited for personal care products, the coated water-dispersible film of the present invention may be advantageously employed in the preparation of a wide variety of consumer products other than personal care products.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and the scope of the appended claims.

EXAMPLE 1

Several versions of this two-layer composition were prepared by coating various grades of REXTAC® amorphous polyalphaolefin resins from Rexene Corporation (Rexene Products Division, Dallas, Tex.) onto a polyethylene oxide film. A second set of samples were prepared from various blends of Rexene resins. Because of thermal limitations of the current polyethylene oxide film, the polyalphaolefin coating was applied with an Acumeter Laboratories Inc. (White Bear Lake, Minn.) precision slot die coater to release paper, and then transferred to the polyethylene oxide substrate. Coated substrates were prepared in the laboratory on a bench-scale slot coater, and in research trials at May Coating Technologies (St. Paul, Minn.). Compositions with polyalphaolefin coating thicknesses ranging from 0.5 to 2.0 mil thickness were prepared.

The poly(ethylene oxide) film used as a substrate was roughly 1.2 mil thick, and had been prepared from resin compounded and pelletized at Planet Polymer Technologies, Inc. (San Diego, Calif. 92131).

The barrier properties of these films were then tested in the laboratory with a modified Cobb's test. In the standard Cobb's test for water uptake in a film (American Society for Testing and Materials [Philadelphia, Pa.] D3285, Technical Association of the Pulp and Paper Industry T441), a fixed surface area of film, clamped under a steel ring, is held under a pool of water, standing at 1 centimeter depth, for a fixed time; the weight gain in the film due to water absorption from the initial dry state to the final, blotted-dry state, is measured. In these experiments, the Cobb's test was modified from a weight-gain method to a visual-indicator test by introducing a layer of pH paper (Hydrion paper for range 3.5 to 5.5 pH, Hydrion Papers Inc. [Brooklyn N.Y. 11210]) under the film. The pH paper turns from orange to green-green/blue when exposed to water and saline solution; the pH paper changes color in the same manner when exposed to a wetted polyethylene oxide film laying on top of it. The color change gave a visual indication of time at which water permeated through the barrier coating and then wetted the polyethylene oxide substrate. The time for water to permeate through the coated film was monitored as a function of film thickness with distilled water as the test fluid.

As a measure of water-sensitivity and dispersability of the coated films, their wet strength was also tested. A one-inch by four-inch sample of film was clamped by the short sides in a Vitrodyne V-1000 mini tensile tester from Chattilone (Greensboro, N.C.) and then submerged, clamps and all, in a beaker of fluid. After 30 seconds, the sample was pulled apart and the peak load measured.

After screening work on the lab coater, three Rexene resins, RTE32, RT2535, and RT2315 were used in a research trial. Each of the three Rexene polymers had a melt viscosity at 190° C. of between about 400 to about 10,000 cps. Coating of polyalphaolefin layers having thicknesses of approximately 0.5 mil, 0.75 mil, and 1.0 mil were prepared. For comparison, a polyethylene-like barrier coating on PEO was also tested. For this sample the same PEO was coextruded with PRIMACOR 1430 from Dow Chemical (Midland, Mich.). The samples were assessed by the peak load in a tensile pull after a 30 second soak. The results are set forth in Table 1.

TABLE 1

| Coating Resin | Thickness (mil) | Peak Load (g/in) |
| --- | --- | --- |
| RT2315 | 1 | 63 |
| RT2315 | 0.8 | 51 |
| RT2315 | 0.4–0.5 | 41 |
| RT2315, with IR heater | 0.4–0.5 | 36 |
| RT2535 | 1.2 | 49 |
| RT2535 | 1 | 38 |
| RT2535 | 0.8 | 36 |
| RT2535 | 0.4 | 32 |
| RTE32 | 0.8–1 | 116 |
| RTE32 | 0.75 | 72 |
| RTE32 | 0.5 | 60 |
| PRIMACOR 1430 | 1.3 | 434 |

Most of the samples of the thickest coating held up against water in a Cobb barrier test for at least 15 minutes. The few failures came from point defects (holes) in the coating. The barrier performance of the thinner coatings was limited by such defects. As can be seen from Table 1, wet strengths (peak loads) for the thickest coatings ranged from 120 grams to 35 grams per one-inch width. This is compared to the PRIMACOR coating which had a substantially higher peak load and, therefore, would not be flushable. The RT2315 polymer (having a viscosity of about 3500 at 190° C.) provided the optimal balance of barrier and wet strength.

EXAMPLE 2

A barrier coating was prepared. The barrier coating comprised a 90/10 blend, by weight, of a coating-grade polyalphaolefin, REXTAC® RT2730 or RT2330 (each having a melt viscosity of about 3000 cps at 190° C.) with a low molecular weight paraffin wax, VYBAR® 253. The blend was coated into a base film of poly(ethylene oxide). The blend was applied to produce a final coating thickness of about 1 mil. Two different thicknesses of PEO were used: PEOB with a film thickness of 0.8 mil and PEOC with a film thickness of 0.5 mil. The barrier properties of these films were then tested in the laboratory with the modified Cobb's test set forth in Example 1. As a measure of water-sensitivity and dispersability of the coated films, their wet strength was also tested. A one-inch by four-inch sample of film was clamped by the short sides in a Vitrodyne V-1000 mini tensile tester from Chattilone and then submerged, clamps and all, in a beaker of fluid. After 30 seconds, the sample was pulled apart and the peak load measured. The samples were assessed by the peak load in a tensile pull after a 30 second soak. The results are set forth in Table 2.

TABLE 2

| Coating Resin | Substrate | Peak Load (g/in) |
| --- | --- | --- |
| RT2730/V253 90/10 | PEOB | 27 |
| RT2330/V253 90/10 | PEOB | 39 |
| RT2730/V253 90/10 | PEOC | 26 |
| RT2330/V253 90/10 | PEOC | 33 |

In this example, almost all of the coated films held up against water in the modified Cobb barrier test for at least 2 hours. However, as shown in Table 2, the films, when submersed in water for 30 seconds, quickly lost their wet strength such that they were easily flushable.

It is to be understood that the above-disclosed embodiments are merely illustrative and are not intended to limit the scope of the invention. On the contrary, other embodiments will become obvious to one skilled in the art in light of the disclosure of the present invention and all such obvious variations are contemplated within the scope of the appended claims.

We claim:

1. A method of making a flushable film having barrier properties, said method comprising:

providing a water-dispersible substrate layer; and applying a coating of hydrophobic, low molecular weight amorphous poly(alpha-olefin), wherein the coating comprises at least one poly(alpha-olfin) having a melt-viscosity of about 400 to about 10,000 cps at 190 ° C., onto a surface of the flushable film, wherein the coating adheres to the water-dispersible substrate layer and provides barrier properties to the film.

2. The method of claim 1, wherein the low molecular weight amorphous poly(alpha-olefin) has a number-average molecular weight of less than about 2800.

3. The method of claim 1, wherein the hydrophobic, low molecular weight amorphous poly(alpha-olefin) has a degree of crystallinity of less than about 20 percent.

4. The method of claim 1, wherein the hydrophobic, low molecular weight amorphous poly(alpha-olefin) is admixed with a branched paraffin wax in a ratio of from about 90 percent by weight poly(alpha-olefin) to about 10 percent by weight branched paraffin wax.

5. The method of claim 1, wherein the film has a peak load strength less than about 120 g/inch after being soaked in water for about thirty seconds.

6. The method of claim 1, wherein the film has a peak load strength of less than about 40 g/inch after being soaked in water for about thirty seconds.

7. The method of claim 1, wherein the hydrophobic, low molecular weight amorphous poly(alpha-olefin) is first applied to a carrier substrate and then subsequently transferred to the water-dispersible substrate.

8. The method of claim 1, wherein the water-dispersible substrate is selected from polyalkylene oxide, polythylene oxide, ethylene oxide-propylene oxide copolymer, polymetharcylic acid, polymethacrylic acid copolymer, polyvinyl alcohol, polyethyl oxazoline, polyvinyl methyl ether, polyvinyl alcohol, polyethyl copolymer, methyyl cellulose, ethyl cellulose, hydroxypropyl cellulose, hydroxypropl methyl cellulose, ethyl hydroxyethyl cellulose, methyl ether starch, poly(n-isopropyl acrylamide), poly N-vinyl caprolactam, polyvinyl methyl oxazolidone, polyvinyl methyl oxazolidimone, poly(2-isopropyl-2oxazoline), and poly (2, 4-dimethyl-6-triazinyl ethylene).

9. The method of claim 1, wherein the hydrophobic, low molecular weight amorphous poly(alpha-olefin) is selected from propylene-ethylene copolymers or ethylene-butene copolymers.

* * * * *